(12) United States Patent
Gupta

(10) Patent No.: US 10,869,026 B2
(45) Date of Patent: Dec. 15, 2020

(54) APPARATUS FOR AUGMENTING VISION

(71) Applicant: Amitabha Gupta, Toronto (CA)

(72) Inventor: Amitabha Gupta, Toronto (CA)

( * ) Notice: Subject to any disclaimer, the term of this patent is extended or adjusted under 35 U.S.C. 154(b) by 431 days.

(21) Appl. No.: 15/355,707

(22) Filed: Nov. 18, 2016

(65) Prior Publication Data
US 2018/0143442 A1    May 24, 2018

(51) Int. Cl.
*H04N 13/344* (2018.01)
*G02B 27/01* (2006.01)
*A61M 11/04* (2006.01)
*A61M 11/00* (2006.01)
*A61M 11/02* (2006.01)

(52) U.S. Cl.
CPC ........ *H04N 13/344* (2018.05); *A61M 11/005* (2013.01); *A61M 11/02* (2013.01); *A61M 11/042* (2014.02); *G02B 27/017* (2013.01); *G02B 27/0172* (2013.01); *A61M 2202/04* (2013.01); *A61M 2205/33* (2013.01); *A61M 2205/50* (2013.01); *A61M 2205/75* (2013.01); *A61M 2205/8206* (2013.01); *G02B 2027/014* (2013.01); *G02B 2027/0134* (2013.01); *G02B 2027/0138* (2013.01); *G02B 2027/0147* (2013.01)

(58) Field of Classification Search
None
See application file for complete search history.

(56) References Cited

U.S. PATENT DOCUMENTS

| | | | |
|---|---|---|---|
| 8,842,166 B2 * | 9/2014 | Ito | A63F 13/65 348/47 |
| 8,957,835 B2 | 2/2015 | Hoellwarth | |
| 9,918,066 B2 * | 3/2018 | Schneider | G01B 11/245 |
| 10,395,428 B2 * | 8/2019 | Stafford | A63F 13/537 |
| 2010/0045783 A1 * | 2/2010 | State | G02B 27/017 348/53 |
| 2011/0050546 A1 | 3/2011 | Swartz, Jr. et al. | |
| 2011/0050864 A1 * | 3/2011 | Bond | G06T 7/579 348/51 |
| 2011/0304700 A1 * | 12/2011 | Ito | A63F 13/65 348/47 |
| 2012/0038796 A1 * | 2/2012 | Posa | H04N 5/23296 348/240.2 |
| 2012/0098972 A1 * | 4/2012 | Hansen | H04N 5/2258 348/164 |
| 2012/0113228 A1 * | 5/2012 | Konno | H04N 13/239 348/47 |
| 2013/0050065 A1 | 2/2013 | Shimizu | |

(Continued)

FOREIGN PATENT DOCUMENTS

| | | |
|---|---|---|
| WO | 2014/100891 | 7/2014 |
| WO | 2015/134733 | 9/2015 |

*Primary Examiner* — Patrick F Marinelli
(74) *Attorney, Agent, or Firm* — Rowand LLP

(57) ABSTRACT

A head-mounted display is disclosed. The head-mounted display includes: a housing adapted to be worn on a user's head, the housing defining a partially enclosed chamber which covers the user's eyes when the housing is worn by the user; at least one display unit mounted in the chamber; a processor coupled to the at least one display unit; and a humidifier coupled to the housing, the humidifier being configured to controllably increase moisture in the chamber.

8 Claims, 6 Drawing Sheets

(56) References Cited

U.S. PATENT DOCUMENTS

| | | | |
|---|---|---|---|
| 2013/0235086 A1* | 9/2013 | Otake | H04N 5/23293 |
| | | | 345/660 |
| 2013/0235169 A1* | 9/2013 | Kato | G02B 27/01 |
| | | | 348/53 |
| 2013/0329190 A1 | 12/2013 | Lewis et al. | |
| 2014/0028802 A1* | 1/2014 | Hendrickson | H04N 13/275 |
| | | | 348/47 |
| 2014/0136098 A1* | 5/2014 | Stroila | G01S 5/0027 |
| | | | 701/408 |
| 2015/0062165 A1* | 3/2015 | Saito | G02B 27/017 |
| | | | 345/633 |
| 2016/0133051 A1* | 5/2016 | Aonuma | G06T 19/006 |
| | | | 345/633 |
| 2016/0156849 A1* | 6/2016 | Baritompa | G02B 7/08 |
| | | | 348/240.1 |
| 2016/0191898 A1* | 6/2016 | Xu | H04N 13/239 |
| | | | 348/47 |
| 2016/0320623 A1* | 11/2016 | Miyao | G02B 27/0172 |
| 2017/0039772 A1* | 2/2017 | Mukawa | G02B 3/12 |
| 2017/0053450 A1* | 2/2017 | Rodriguez | G06T 7/579 |
| 2017/0178408 A1* | 6/2017 | Bavor, Jr. | G06F 3/013 |
| 2017/0287222 A1* | 10/2017 | Fujimaki | G06T 19/006 |
| 2017/0299842 A1* | 10/2017 | Posa | G02B 7/06 |
| 2017/0358141 A1* | 12/2017 | Stafford | G02B 27/017 |
| 2017/0359562 A1* | 12/2017 | Schneider | G01B 11/245 |
| 2018/0143442 A1* | 5/2018 | Gupta | A61M 11/042 |
| 2018/0176532 A1* | 6/2018 | Gallo | H04N 13/271 |
| 2018/0267605 A1* | 9/2018 | Border | G06F 3/013 |
| 2019/0122335 A1* | 4/2019 | Rasmussen | G01C 21/32 |
| 2020/0145644 A1* | 5/2020 | Cordes | H04N 5/23238 |

* cited by examiner

APPARATUS FOR AUGMENTING VISION

TECHNICAL FIELD

The present disclosure relates to devices for augmenting vision and, in particular, to head-mounted display devices for providing electronically augmented images or videos.

BACKGROUND

Low vision refers to a state of reduced vision which cannot be corrected with medical treatment, surgery, or conventional glasses and contact lenses. Common causes of low vision include macular degeneration, diabetic retinopathy, glaucoma, cataracts, and eye injuries. Low vision is often characterized by partial vision, visual field loss (e.g. blind spots, tunnel vision), or legal blindness. People suffering from low vision experience significant difficulty with everyday tasks, such as general mobility and reading.

Various low vision aids are known. Low vision optical devices, such as stand or handheld-magnifiers, magnifying reading glasses, clip-on loupes and spectacle-mounted telescopes, can provide increased magnification powers and prescription strengths as well as higher-quality optics. These devices are usually task-specific, and different devices may be prescribed for different tasks.

A common condition experienced by people with low vision is eye dryness. Dry eye syndrome, or DES, is an eye disease which can be caused by decreased tear production or increased tear film evaporation. Aging is also a common cause of dry eyes as tear production decreases with age. Use of low vision aids can exacerbate the pain and discomfort attributable to dry eyes.

BRIEF DESCRIPTION OF DRAWINGS

Reference will now be made, by way of example, to the accompanying drawings which show example embodiments of the present application and in which.

Like reference numerals are used in the drawings to denote like elements and features.

DETAILED DESCRIPTION OF EXAMPLE EMBODIMENTS

In an aspect, the present disclosure describes a head-mounted display designed to facilitate alleviation of eye dryness. The head-mounted display includes: a housing adapted to be worn on a user's head, the housing defining a partially enclosed chamber which covers the user's eyes when the housing is worn by the user; at least one display unit mounted in the chamber; a processor coupled to the at least one display unit; and a humidifier coupled to the housing, the humidifier being configured to controllably increase moisture in the chamber.

In another aspect, the present disclosure describes a head-mounted display capable of providing stereoscopic images of a scene. The head-mounted display includes: a first camera for capturing a left viewpoint image of a scene; a second camera for capturing a right viewpoint image of the scene, the second camera having a field of view at least partially overlapping a field of view of the first camera; a first display unit and a second display unit; and a processor coupled to the first camera, the second camera, the first display unit and the second display unit, the processor being configured to: receive a first image from the first camera; receive a second image from the second camera; identify a region of interest which is included in both the first image and the second image; select a first sub-image of the first image such that the region of interest is centrally positioned in the first sub-image; select a second sub-image of the second image such that the region of interest is centrally positioned in the second sub-image; display the first sub-image on the first display unit; and display the second sub-image on the second display unit.

Other example embodiments of the present disclosure will be apparent to those of ordinary skill in the art from a review of the following detailed description in conjunction with the drawings.

Figure 1A:
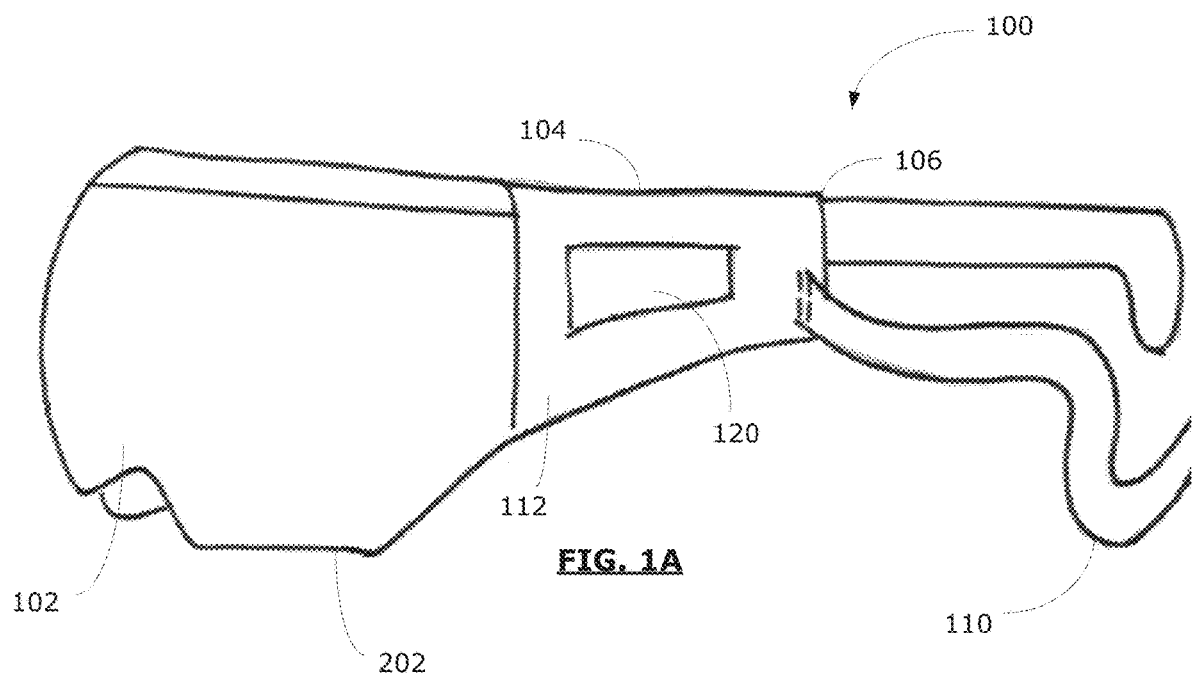
FIG. 1A is a perspective view of a head-mounted display in accordance with an example embodiment of the present disclosure.

Reference is first made to FIG. 1, which shows a perspective view of an example head-mounted display (HMD) 100. The HMD 100 is configured to be worn on a user's head and includes at least one display optic which is viewable by the user when the HMD 100 is worn. The display optic associated with the HMD 100 may provide displays of electronically generated images and/or videos for viewing by a user of the HMD 100. In at least some embodiments, the HMD 100 may implement an augmented vision system for use by visually impaired persons. The HMD 100 may adapt various image enhancement techniques to generate augmented images of real world environments which can be seen by persons with low vision. In particular, the HMD 100 may be configured to process images of a user's surroundings in real-time and apply digital enhancements to the images which are appropriate for the particular visual impairments experienced by the user.

In some embodiments, the HMD 100 may be an optical head-mounted display (OMHD). That is, the HMD 100 may reflect projected images while also allowing a user to see through the display. For example, various notifications, text, and images may be superimposed on a real world view using the HMD 100. As a result, the HMD 100 may be suitable for providing, for example, immersive and/or mobile augmented reality.

The HMD 100 may include a front cover 102 and a frame 104. The front cover 102 may be coupled to the frame 104 to form the front surface of the HMD 100. When the HMD 100 is worn on a user's head, the front cover 102 may be positioned in front of the user's face such that it substantially covers the user's eyes. In the example of FIG. 1, the front cover 102 is shaped as a curved surface which generally follows the contour of a user's face. In some other embodiments, the front cover 102 may have a planar or substantially planar surface. The front cover 102 may comprise a single cover body or it may be formed from multiple pieces that are combined and held together by frame 104. For example, the front cover 102 may include a separate cover portion for each of left and right eyes of a user, such that the cover portions align with each respective eye and are held in laterally spaced relation to each other by the frame 104.

In at least some embodiments, the front cover 102 may be translucent or completely opaque. The inner surface of the front cover 102 may be colored a dark color to provide viewing contrast with respect to display units mounted in the HMD 100. For example, the inner surface of the front cover 102 may be colored black to contrast with the portions of display screens disposed in the interior of the HMD 100 which are viewable by a user of the HMD 100. The display units of the HMD 100 will be described in greater detail below. The front cover 102 may be formed from relatively light and rigid material including, for example, glass, plastic, ceramic, or metal.

The frame 104 forms a support structure for the HMD 100. In at least some embodiments, the frame 104 comprises sidewalls which support and maintain the front cover 102 in spaced relation to a user's face when the HMD 100 is worn by the user. For example, as shown in the example of FIG. 1, the frame 104 may include a left frame member 106 and a right frame member which extend from an inner side of the front cover 102. The left and right frame members are generally perpendicular to a plane defined by the front cover 102 and support the left and right sides of the front cover 102, respectively. In particular, the left frame member 106 and right frame member may be in parallel spaced relation to each other.

As a further example, the frame 104 may be a spacer which extends from an inner side of the front cover 102. A spacer may comprise a substantially continuous sidewall that extends away from the front cover 102. The spacer may define an inner cavity configured to hold, for example, display units of the HMD 100. The spacer may be shaped to accommodate the contour of a user's face. In particular, when the HMD 100 is worn by a user, the spacer may make contact with the user's face such that the front cover 102 is maintained a fixed distance away from the user's face. In some embodiments, a flexible seal member (e.g. constructed of rubber, foam, etc.) may be attached to a free end of the spacer to form a seal between the spacer and the user's face. For example, the seal member may extend along the perimeter of the free end of the spacer such that it rests against the user's face when the HMD 100 is worn. The seal member may accommodate positioning of the HMD 100 relative to the user's head while also serving to prevent ambient light from entering an interior chamber of the HMD 100 and affecting images displayed by the HMD 100.

The frame 104 may be integrally formed with the front cover 102 (as in the example of FIG. 1), or it may be separable from the front cover 102. In some embodiments, the front cover 102 may be a separate component that can be secured to the frame 104 by a suitable attachment mechanism. For example, the front cover 102 and the frame 104 may include interlocking components which allow left and right frame members to engage and be secured to the front cover 102.

The frame 104 and the front cover 102 together define a partially enclosed interior chamber for the HMD 100. In particular, when the HMD 100 is worn by a user, the front cover 102 and the frame 104 cooperate to provide a partial enclosure over a portion of the user's face which is covered by the HMD 100. That is, the front cover 102 and the frame 104 define at least part of the boundaries of an enclosure in the interior of the HMD 100. For example, the frame 104 may comprise a sidewall that is designed for close fit to a user's face and which may reduce or prevent ambient light entering an interior chamber of the HMD 100 enclosed by the front cover 102 and the sidewall. As will be further described below, one or more display units may be mounted in the partially enclosed interior chamber of the HMD 100, and an open end of this interior chamber allows a user to view content displayed by the one or more display units.

As can be seen in FIG. 1, an outer surface 112 of the frame 104 may include one or more input interfaces 120 for the HMD 100. The input interfaces 120 may be removably attached to the outer surface 112 or integrally formed with the frame 104. The input interfaces 120 may allow a user to manually control various functionalities of the HMD 100. For example, input received from a user via the input interfaces 120 may be communicated to a processor associated with the HMD 100 to control or adjust display settings of the HMD 100. Placement of the control elements, such as input interfaces 120, directly on the HMD 100 may allow the HMD 100 to function as a stand-alone device. In particular, an HMD in accordance with embodiments of the present disclosure may be used independently, without any accompanying accessories or physical hubs for controlling the operation of the HMD.

The HMD 100 also includes components which facilitate securing the HMD 100 to a user's head. In at least some embodiments, the HMD 100 includes an adjustable strap 110 which may be used to secure the HMD 100 to a user's face. For example, the strap 110 may be affixed to an outer surface of the frame 104 or the frame 104 may include slots for receiving the strap 110. The strap 110 may be configured to be placed over or around a user's head to secure the HMD 100 when it is in use. In some embodiments in which the frame 104 comprises separate left and right frame members, the HMD 100 may include frame end pieces extending from each of the left and right frame members for mounting on top of a user's ears in order to secure the HMD 100 in place with respect to the user's head.

Figure 1B:
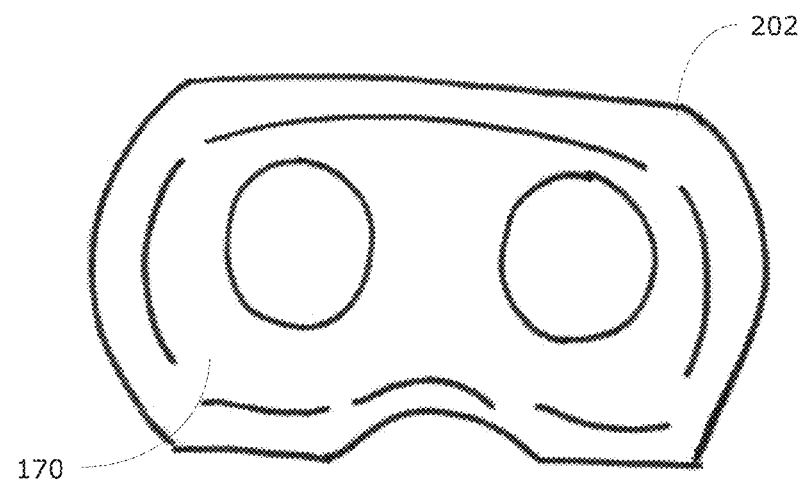
FIG. 1B is a rear view of the example head-mounted display of FIG. 1A.
Figure 2:
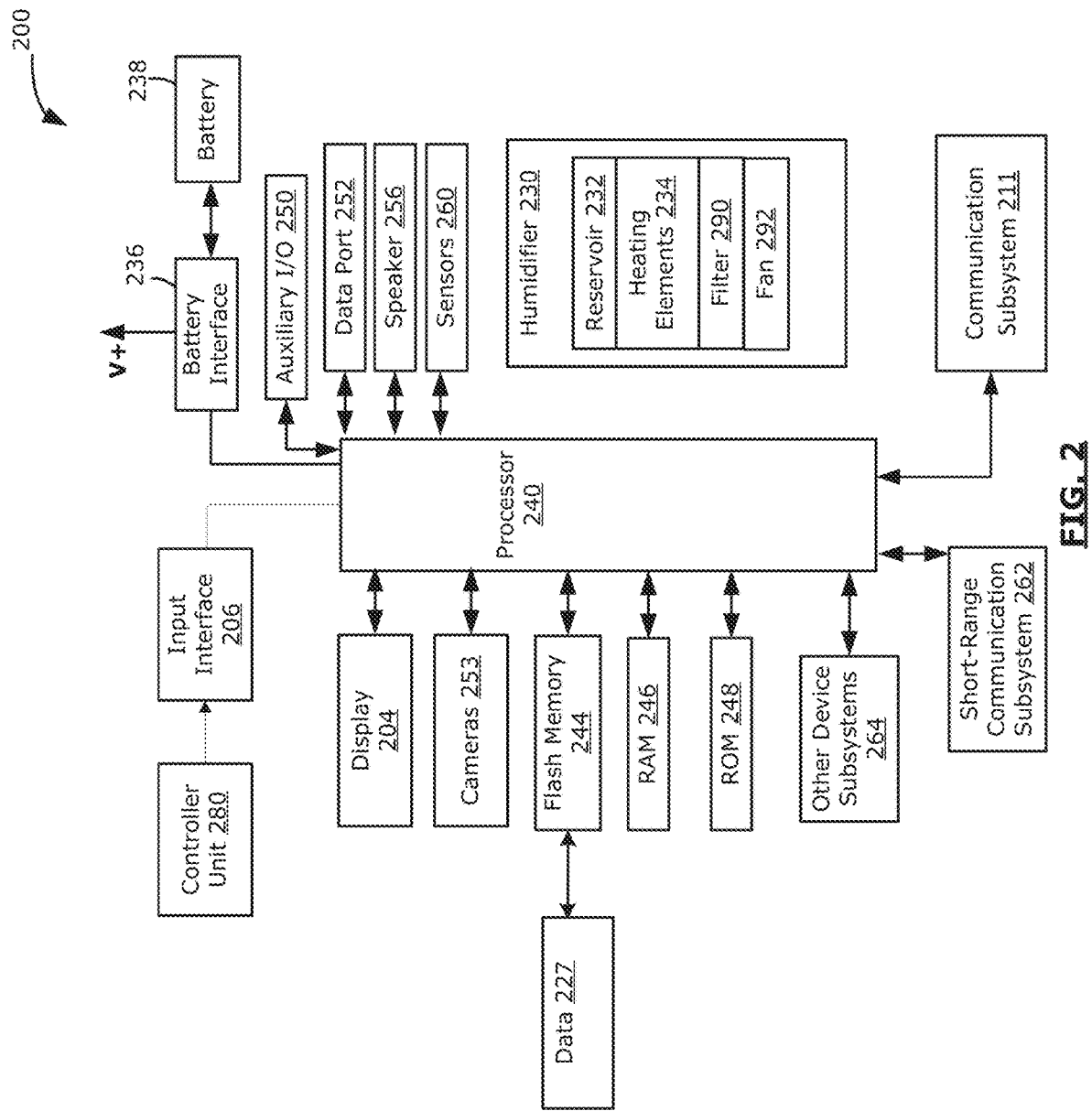
FIG. 2 is a block diagram illustrating components of a head-mounted display in accordance with an example embodiment of the present disclosure.

Reference is now made to FIG. 2, which shows a block diagram illustrating components of an example HMD 200 in accordance with embodiments of the present disclosure. The HMD 200 includes a housing 202 (shown in FIG. 1A) which houses components of the HMD 200. The housing 202 is configured to be worn on a user's head. In particular, at least a portion of the housing 202 may be shaped to generally conform to the contour of a user's face, allowing the housing 202 to be comfortably secured to the user's head when the HMD 200 is in use. The housing 202 includes a front cover and a support frame, such as front cover 102 and frame 104 of FIG. 1, respectively. Internal components of the HMD 200 may be constructed on a printed circuit board (PCB). The HMD 200 includes a controller including at least one processor 240 (such as a microprocessor) which controls the overall operation of the HMD 200. The processor 240 interacts with device subsystems such as a wireless communication subsystem 211 for exchanging radio frequency signals with an external wireless network to perform communication functions. The processor 240 interacts with additional device subsystems including one or more input interfaces 206, flash memory 244, random access memory (RAM) 246, read only memory (ROM) 248, auxiliary input/output (I/O) subsystems 250, a data port 252 (which may be a serial data port, such as a Universal Serial Bus (USB) data port), one or more output interfaces (such as display units 204, which may be liquid crystal displays (LCD), one or more speakers 256, or other output interfaces), a short range communication module 262, and other device subsystems generally designated as 264. Some of the subsystems shown in FIG. 2 perform communication-related functions, whereas other subsystems may provide "resident" or on-device functions.

The HMD 200 includes one or more display units 204. The display units 204 display images for viewing by a user of the HMD 200. The display units 204 are mounted in an interior chamber defined by the housing 202 and are directly viewable when the HMD 200 is worn by a user. In particular, the display units 204 are positioned within the housing 202 such that the display units 204 are disposed directly in front of the user's eyes when the HMD 200 is suitably mounted on the user's head during use. In some embodiments, the display unit 204 may comprise a single display screen centrally positioned within the housing 202. In other embodiments, two separate display screens may be provided, with a display screen disposed in front of each of a user's left and right eyes. For example, two display screens 204 may be mounted in the interior of the housing 202 and positioned in laterally spaced relation to each other such that the centers of the display screens 204 are separated by an appropriate distance (e.g. mean inter-pupillary distance, ranging from approximately 58 millimeters to 70 millimeters). The display screens may use any one of Organic Light Emitting Diode (OLED), Liquid Crystal on Silicon (LCS), virtual retinal display (VRD), or Liquid Crystal Display (LCD) technologies. The display screens may comprise arrays of a plurality of curved mirrors. In some embodiments, the display units 204 may be disposed on an inner surface of the front cover. For example, the display units 204 may comprise screens that are built in to the inner surface of the front cover such that the screens are positioned opposite a user's eyes during use of the HMD 200. Alternatively, the display units 204 may be suspended inside the housing 202 in spaced relation to the inner surface of the front cover.

The processor 240 interacts with the display units 204 and is configured to transmit data for display by the display units 204. In particular, the processor 240 may transmit image and/or video data to the display units 204 for display to a user of the HMD 200. For example, if the display unit 204 comprises two display screens, the processor 240 may generate and provide separate images for each of the display screens. As will be described further below, the images provided to the respective display screens may comprise left and right eye views of a user's real world environment, seen using the HMD 200.

The communication subsystem 211 includes a receiver, a transmitter, and associated components, such as one or more antenna elements, local oscillators, and a processing module such as a digital signal processor (DSP). The antenna elements and may be embedded or internal to the HMD 200 and a single antenna may be shared by both receiver and transmitter. The particular design of the wireless communication subsystem 211 depends on the external wireless network in which the HMD may be configured to operate.

In some embodiments, the auxiliary I/O subsystems 250 may include an external communication link or interface such as, for example, an Ethernet connection. The HMD 200 may include other wireless communication interfaces for communicating with other types of wireless networks; for example, a wireless network such as an orthogonal frequency division multiplexed (OFDM) network.

The HMD 200 may store data 227 in an erasable persistent memory which, in one example embodiment, is the flash memory 244. The data 227 may include user profile information and user preferences with respect to image display settings, such as magnification level and image enhancement and control modes (e.g. brightness, contrast, etc.). The data 227 may, in some embodiments, include metadata storing information about images generated and/or displayed using the HMD 200. The metadata and the images may be stored together or separately. The data 227 may also include such information as device identification data, usage history, and profiles of connected devices.

The data port 252 may be used for synchronizing the HMD 200 with one or more external computer systems. The data port 252 enables a user to set preferences through an external device or software application and extends the capabilities of the HMD 200 by providing for information or software downloads to the HMD 200 other than through an external wireless network. For example, the processor 240 of the HMD 200 may receive image and/or video data for display on the display units 204 via wired USB connections to external devices, such as a computer or camera. In at least some embodiments, the HMD 200 may be synchronized wirelessly with external systems and devices, for example, via the communication subsystem 211 and/or the short range communication module 262.

The HMD 200 includes a battery 238 as a power source, which is typically one or more rechargeable batteries that may be charged, for example, through charging circuitry coupled to a battery interface 236. The battery 238 provides electrical power to at least some of the electrical circuitry in the HMD 200, and the battery interface 236 provides a mechanical and electrical connection for the battery 238. The battery interface 236 is coupled to a regulator (not shown) which provides power V+ to the circuitry of the HMD 200.

The short range communication module 262 provides for communication between the HMD 200 and different systems or devices. For example, the short range communication module 262 may include an infrared device and associated circuits and components, or a wireless bus protocol compliant communication mechanism such as a Bluetooth® communication module to provide for communication with similarly-enabled systems and devices.

The HMD 200 includes one or more cameras 253. The cameras 253 are capable of acquiring camera data such as images in the form of still photographs and/or motion video. The camera data may be captured in the form of an electronic signal which is produced by an image sensor. In at least some embodiments, the HMD 200 includes two cameras 253 configured to capture left and right viewpoint images of a real world scene. That is, a first camera of the HMD 200 may capture an image corresponding to a left eye view of a scene and a second camera of the HMD 200 may capture an image corresponding to a right eye view of the same scene. As a result, the cameras 253 may provide suitable images for generating binocular views of a scene. In some other embodiments, the HMD 200 may include a single camera 253. For example, a camera 253 that is centrally disposed in the HMD 200 may be configured to capture images which may be displayed as single images or which may be digitally modified to generate two different images (i.e. left and right images) for presentation to the respective eyes of a user. The captured images may also be modified non-digitally; for example, a camera view may be split into a left and right view using various arrangements of of mirrors and/or prisms.

The cameras 253 are mounted in the housing 202 and are front-facing. That is, the cameras 253 are mounted in such a manner that, when the HMD 200 is worn by the user, the cameras 253 are directed to scenes in front of the user. In at least some embodiments, the cameras 253 may be integrated into the front cover. For example, the front cover may be at least partially translucent and allow sufficient light to enter image sensors associated with cameras 253 positioned inside the front cover. As another example, the cameras 253 may be embedded into the front cover such that the lens covering the image sensors of the cameras 253 are substantially flush with an outer surface of the front cover. The cameras 253 may alternatively be mounted directly on the outer surface of the front cover.

In some embodiments, each camera 253 may be coupled to an actuator or motor for electrically displacing the camera 253 with respect to the housing 202. The actuator or motor may be controlled by signals provided by control circuitry of the HMD 200 or a remote control circuitry (e.g. an external device that is connected to the HMD 200). A user of the HMD 200 may manually control an actuator/motor to change the relative position or line of sight of an associated camera, or the actuator/motor may be engaged automatically in response to predetermined triggers (e.g. detection of eye movement via gaze tracking).

The cameras 253 may be coupled directly with the processor 240 which controls the cameras. In some embodiments, the cameras 253 may include dedicated image signal processors which may provide at least some camera-related functions. For example, an image signal processor of camera 253 may be configured to provide, among others, autofocusing, sensitivity and brightness control, or magnification functions. Various functions and features of a dedicated camera application or software module may, in some embodiments, be provided, in whole or in part, by an image signal processor.

The HMD 200 may also include one or more on-board sensors 260. For example, the HMD 200 may include a gyroscope and/or an accelerometer. The HMD 200 may also include eye- or gaze-tracking sensors/cameras for measuring the motion of eyes relative to a user's head and the direction or point of gaze. For example, one or more infrared-sensitive cameras may be mounted in the interior of the housing 202 to track movement of a user's eyes based on known techniques, such as corneal-reflection-based eye tracking. In at least some embodiments, the HMD 200 includes a thermometer and/or a hygrometer inside the housing 202. That is, sensors may be provided in the HMD 200 for measuring the temperature or moisture content in the interior space of housing 202.

The housing 202 of HMD 200 defines an interior space, as shown in FIG. 1B. For example, the front cover and support frame may define an interior cavity for the housing 202. In particular, the interior of the housing 202 includes an at least partially enclosed chamber 170. The front cover and support frame may define the front and side walls, respectively, of the chamber 170. When the HMD 200 is worn by a user, the HMD 200 can be positioned relative to the user's head such that at least a portion of the chamber 170 is disposed directly in front of the user's eyes. The chamber 170 provides an unobstructed visual pathway extending between the display units 204 and the user's eyes. For example, the display units 204 may be mounted in the chamber 170 and positioned to face towards the open end of the chamber 170. Alternatively, the display units 204 may be built-in to the front cover and the chamber 170 may be located adjacent to the display units 204.

In at least some embodiments, the chamber 170 is partially enclosed by components of the housing 202 and defines an open end through which the display units 204 can be viewed. For example, the front cover, support frame and a seal member attached to a free end of the support frame may form a sealed enclosure 170 between the housing 202 and a user's face when the HMD 200 is worn during use. In some other embodiments, the open end of chamber 170 may remain partially exposed when the HMD 200 is worn by a user.

As the chamber 170 is at least partially closed off during use of the HMD 200, the chamber 170 may not be provided with sufficient ventilation. When the HMD 200 is in use, the humidity in the chamber 170 of housing 202 may drop to low levels. For example, the components of the HMD 200 may become heated after an extended period of use, leading to an increase in temperature in the chamber 170. Moreover, thermal radiation normally emitted by a user's body may become partially trapped in the chamber 170, leading to further increases in temperature. This low humidity in the chamber 170 may cause dry, irritated eyes as a result of increased rate of tear evaporation. The low humidity may also exacerbate the effects of various eye diseases or disorders such as, for example, dry eye syndrome (DES). The problems of low humidity levels may be especially more pronounced in the context of a vision aid device, such as the HMD 200, which may be used regularly for normal everyday tasks. For example, the HMD 200 may be used for activities (e.g. prolonged reading, watching videos, etc.) that require visual concentration which, as a result of reduced rate of blinking, can compound the effects of dry eyes. In particular, low humidity in the interior of HMD 200 may act as a significant barrier to comfortable and satisfactory use of the HMD 200.

The HMD 200 includes a humidifier 230. The humidifier 230 may be remotely coupled to the housing 202 or integrated into one or more components of the housing 202 (such as the support frame). For example, the humidifier 230 may be integral with the housing 202 or it may be a component which may be removably attached to the housing 202. In some embodiments, the housing 202 may be configured to receive the humidifier 230 as an add-on component, and the humidifier 230 may be secured to the housing 202 and connected to, at least, the processor 240. The humidifier 230 is designed to regulate the humidity level in the interior of the housing 202 of HMD 200. In particular, the humidifier 230 is configured to controllably increase moisture in the partially enclosed chamber 170 of housing 202. The humidifier 230 is fluidly connected to the chamber 170. Vapor steam or liquid particles released from the humidifier 230 can be transmitted through an outlet of the humidifier 230 and spread into the chamber 170. For example, the humidifier 230 may be integrated into the support frame, and a permeable filter member substantially covering an outlet of the humidifier 230 may be positioned on an inner surface of a sidewall of the support frame to regulate the transmission of vapor and/or liquid particles into the chamber 170. A plurality of apertures may be defined on one or more sidewalls of the housing 202 to permit vapor or water molecules generated by the humidifier 230 to enter the chamber 170. For example, the apertures may be located adjacent to the outlet of the humidifier 230. In some embodiments, all or part of the humidifier 230 may be removably mounted in the housing 202. For example, one or more components of the humidifier 230 may be removed from the housing 202 and replaced. The humidifier 230 may itself be a portable, add-on device which can be optionally coupled to the housing 202.

In at least some embodiments, operation of the humidifier 230 is at least partly controlled by the processor 240. For example, electronic control circuitry of the humidifier 230 may be coupled to and controlled by the processor 240. Accordingly, the humidifier 230 may be actuated upon receiving instructions from the processor 240 and operated in accordance with the instructions (e.g. settings, parameters, etc.). The humidifier 230 may also be manually operated by a user of the HMD 200. For example, the housing 202 may be provided with an input interface which can be directly engaged by a user to control operation of the humidifier 230. In some embodiments, a slidable or press control switch may be integrated into the housing 202.

The humidifier 230 may be configured to employ any one or more of various techniques for increasing the moisture content of the air in chamber 170. In at least some embodiments, the humidifier 230 may be an evaporative humidifier. The humidifier 230 may contain or be coupled to a reservoir 232 for storing a liquid. The liquid may be water, an aqueous solution containing medicaments for treating/preventing eye dryness, or a solution containing one or more lubricating drops and ointments. The humidifier 230 may also include a fan 292. The liquid from the reservoir 232 may be channeled to and absorbed by a wick filter, and the fan 292 of the humidifier 230 may blow air onto the wick in order to facilitate evaporation of the liquid. As a result, the liquid may be expelled from the humidifier 230 as water vapor, mist or spray.

In at least some embodiments, the humidifier 230 may be configured to heat the liquid stored in the reservoir 232. Applying heat to the liquid can increase the rate of evaporation which, in turn, accelerates increase of moisture in the chamber 170. For example, one or more electric heating elements 234 may be disposed in the reservoir 232 and connected to battery 238 of HMD 200. The power generated by the battery 238 can be supplied to heat the elements 234 and, in turn, the liquid held in the reservoir 232. In some embodiments, the humidifier 230 may include a heat exchanger. For example, a partial heat pipe may be provided in the housing 202 to hold a liquid (e.g. water). The heat pipe may be formed from a thermally conductive material, such as copper or aluminum alloy. The heat pipe can be integrated into or located adjacent to an electronic component of the HMD 200, such as the display unit 204 or processor 240. The heat generated by the electronic component may be conducted into the heat pipe, causing the liquid contained therein to be heated. Eventually, the liquid can be transformed into vapor, which can traverse through the heat pipe to an outlet connected to the chamber 170. As an additional example, a heat sink may be included in the HMD 200. A heat sink, such as a cold plate, is designed to transfer heat from a higher temperature device to a liquid. In some embodiments, the heat sink may comprise a conductive plate which makes contact with a heat-generating electronic component and a liquid (or a reservoir holding the liquid). The heat dissipated by the component is transferred to the liquid, causing the liquid to be heated. Other heat transfer techniques may be acceptable for the present invention. Furthermore, a combination of one or more of the above described mechanisms may be implemented to heat a liquid and cause evaporation.

In yet other embodiments, the humidifier 230 may be an ultrasonic humidifier. An ultrasonic humidifier uses a piezoelectric transducer to generate high-frequency oscillations in a body of water to release water vapor molecules into the surrounding air.

The humidifier 230 may also include a filter 290. The filter 290 may reduce the amount of impurities and/or pathogens that may be released by the humidifier 230. In some embodiments, the filter 290 may be disposed near an outlet of the humidifier 230. The filter 290 may be a wick filter that is configured to absorb liquid from the reservoir 232 and trap any dirt or other particles. The filter 290 will preferably be replaceable or adapted to be cleaned by conventional means.

As described above, the humidifier 230 may be controlled, in part, by the processor 240. In particular, the processor 240 may control, among other variables, the timing, duration and rate of evaporation of liquid from the reservoir 232 using the humidifier 230. The processor 240 is coupled to numerous components of the HMD 200 and may be configured to operate the humidifier 230 automatically according to one or more factors relating to the actual use of the HMD 200. As the HMD 200 provides displays of visual content to a user of the HMD 200, in some embodiments, the operation of the humidifier 230 may depend on parameters relating to the display function of the HMD 200. For example, the humidifier 230 may be automatically actuated after the display unit 204 has been turned on for a predetermined period of time. If a user views content presented on the display unit 204 continuously for a duration exceeding a threshold period, the user may begin to experience eye dryness (for example, due to falling humidity levels within chamber 170). Accordingly, the processor 240 may cause the humidifier 230 to increase the moisture content in the chamber 170. In some cases, eye-tracking technology may be used to detect if and for how long a user is viewing content displayed on the display unit 204.

The content of displayed information may be relevant for determining whether a user is likely to begin experiencing effects of eye dryness. Content such as text or complex video images, which may invite greater visual concentration, can cause earlier onset of eye dryness. In at least some embodiments, the processor 240 may be configured to control operation of the humidifier 230 according to the type of content displayed on the display unit 204. For example, if a prolonged period of textual reading using the HMD 200 is detected, the humidifier 230 may be caused to increase moisture content in the chamber 170 (e.g. greater rate of evaporation of liquid in the reservoir 232). As the actual content displayed by the HMD 200 may continuously change, the processor 240 may be configured to measure a contiguous time period of display of one or more predetermined types of visual content and control the operation of the humidifier 230 based, at least in part, on these measurements.

In some embodiments, a hygrometer may be used to measure the humidity level inside chamber 170. The hygrometer readings may influence the operation of the humidifier 230. For example, if the humidity level falls below a certain threshold value, the processor 240 may be configured to actuate the humidifier 230 or increase the rate of evaporation in the chamber 170. Alternatively, the humidifier 230 may be actuated if the humidity level remains below a threshold value for a predefined period of time.

Figure 3:
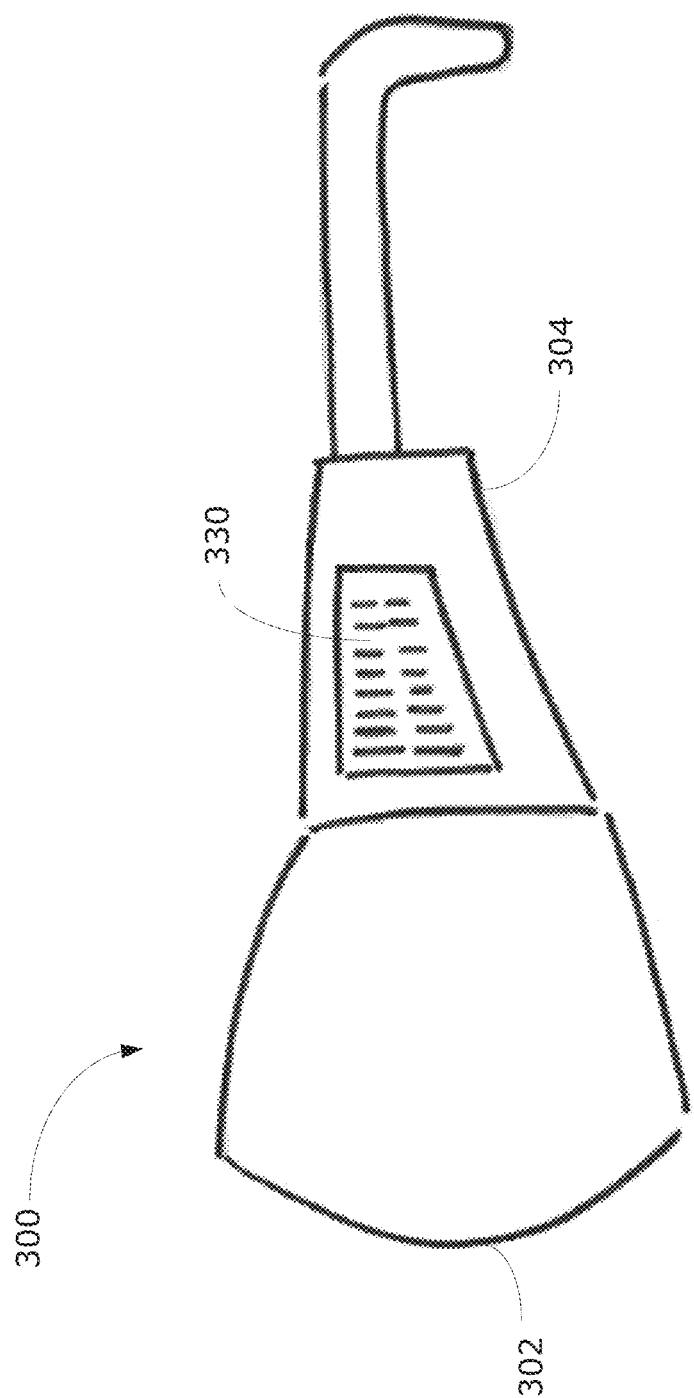
FIG. 3 is a side cross-sectional view of the example head-mounted display of FIG. 1, which shows a humidifier for the head-mounted display in accordance with an example embodiment of the present disclosure.

FIG. 3 shows a side cross-sectional view of an example HMD 300. A humidifier 330 is integrated into one or both of the support frame members 304 which are connected to and extend away from the front cover 302. A filter comprising a plurality of apertures overlays an outlet portion of the humidifier 330. In the example HMD of FIG. 3, the outlet of the humidifier 330 has an elongate shape and generally extends along an inner surface of a support frame member 304. It should be noted that the outlet of the humidifier 330 may be formed in a different shape, such as a circle, rectangle or ellipse.

In at least some embodiments, the processor 240 and associated electronics of one or more device subsystems of the HMD 200 may be integrated into the front cover and/or support frame of housing 202. In particular, the on-board processor 240 may perform various tasks, such as image enhancement, data processing, etc., and execute the software modules stored in memory of the HMD 200, without relying on additional processing capacity from external systems or devices.

The input interface 206 may include a controller unit 280. In some embodiments, the controller unit 280 may comprise a physical interface, such as a panel or touchscreen, which is directly coupled to the housing 202. For example, the controller unit 280 may be a panel containing a plurality of depressible buttons that correspond to various functionalities which can be implemented by the HMD 200. As another example, the controller unit 280 may comprise a touch-sensitive overlay (i.e. a touch-sensitive input surface overlaying a display). The processor 240 interacts with the controller unit 280 to receive instructions manually input by a user of the HMD 200 using the controller unit 280. In at least some embodiments, the controller unit 280 can be used to control the display of information on the display unit 204. For example, the controller unit 280 may be used to navigate a graphical menu that is displayed on the display unit 204. As another example, the controller unit 280 can be used to move a displayed cursor or any other indicator user interface element for selecting and highlighting various regions of displayed images on the display unit 204.

In some embodiments, a user can indicate settings or parameters to apply to images that are displayed by the HMD 200 using the controller unit 280. For example, the controller unit 280 may provide options to select one or more image enhancements to apply to images that are captured by cameras 253 of HMD 200. The image processing options for the HMD 200 may include, among others, image magnification/minification, brightness adjustment, contrast reversal, color changes, edge enhancement, image remapping, and text extraction.

Method for Simulating Convergence on a Head-Mounted Display

Figure 4:
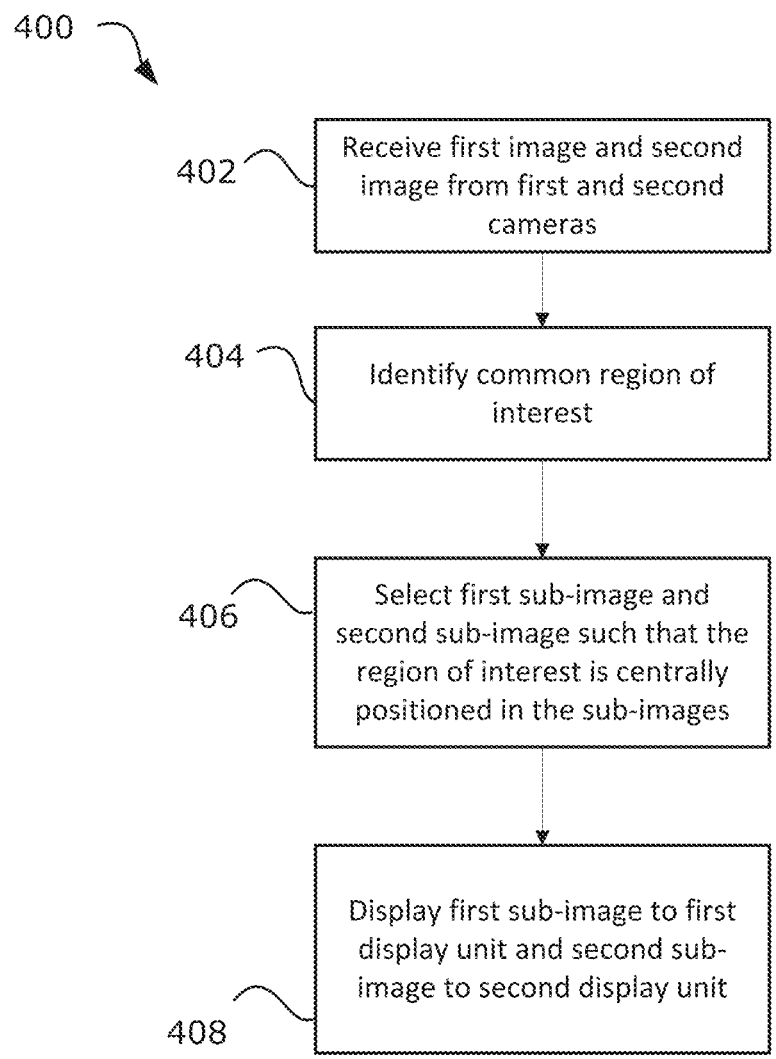
FIG. 4 is a flowchart of an example method for simulating convergence on a head-mounted display.

Reference is now made to FIG. 4, which shows an example method 400 for simulating convergence using an HMD. An HMD in accordance with example embodiments of the present disclosure can be used to simulate the effects of binocular vision. In particular, an HMD may be used to generate the illusion of depth in an image by means of stereopsis. Two separate imaging units (e.g. cameras) may be mounted in spaced relation to each other on the HMD. More specifically, a first imaging unit and a second imaging unit, which have overlapping fields of view, may be mounted on the HMD and directed towards scenes in front of a user wearing the HMD. The first imaging unit and the second imaging unit may be configured to capture a left viewpoint image and a right viewpoint image of a scene, respectively, as seen by a user of the HMD.

In at least some embodiments, one or more steps of method 400 are implemented by a processor of an HMD, such as processor 240 of FIG. 2. In particular, the processor of the HMD is coupled, at least, to a first imaging unit, a second imaging unit, a first display unit and a second display unit. In some embodiments, the method 400 may be wholly or partly implemented by a processor of an external computing system that is communicably coupled to a processor and/or display unit of the HMD.

In operation 402, a first image from the first camera and a second image from the second camera are received. The first image and the second image are captured substantially simultaneously; that is, the images are captured by the first and second cameras, respectively, at or nearly at the same time. In at least some embodiments, the fields of view of the first camera and the second camera are greater than the fields of view of the first display unit and the second display unit, respectively. The captured images may be stored in a memory associated with the HMD and/or transmitted directly to a processor of the HMD. In operation 404, a region of interest which is common to both the first image and the second image is identified. In at least some embodiments, various feature detection and matching algorithms may be used to identify a common region of interest from the captured images. For example, a plurality of points from the two images can be matched based on extracting local features, matching the features from the images, and retrieving the locations of the corresponding points for each image. In some embodiments, active autofocus (i.e. emission of ultrasonic sound waves or infrared light to measure subject distance) or passive autofocus algorithms (e.g. phase detection or contrast detection) may be employed to identify the common region of interest. For example, the default autofocus systems on the first and second cameras may be used. In some embodiments, a user of the HMD may manually select a region or object of interest based on displays of the images on the first and second display units.

In operation 406, a first sub-image of the first image and a second sub-image of the second image are selected. The first sub-image is selected such that the region of interest is centrally positioned in the first sub-image, and the second sub-image is selected such that the region of interest is centrally positioned in the second sub-image. The selection of the sub-images may depend on the resolution of the first and second display units. For example, a sub-image may be selected such that the region of pixels of the sub-image matches the resolution of the corresponding display unit, providing the effect of a magnification of the sub-image. That is, the sub-images may be displayed at magnification levels that are greater than the magnification levels for the first image and the second image, respectively. In operation 408, the first sub-image is displayed on the first display unit and the second sub-image is displayed on the second display unit.

Figure 5A:
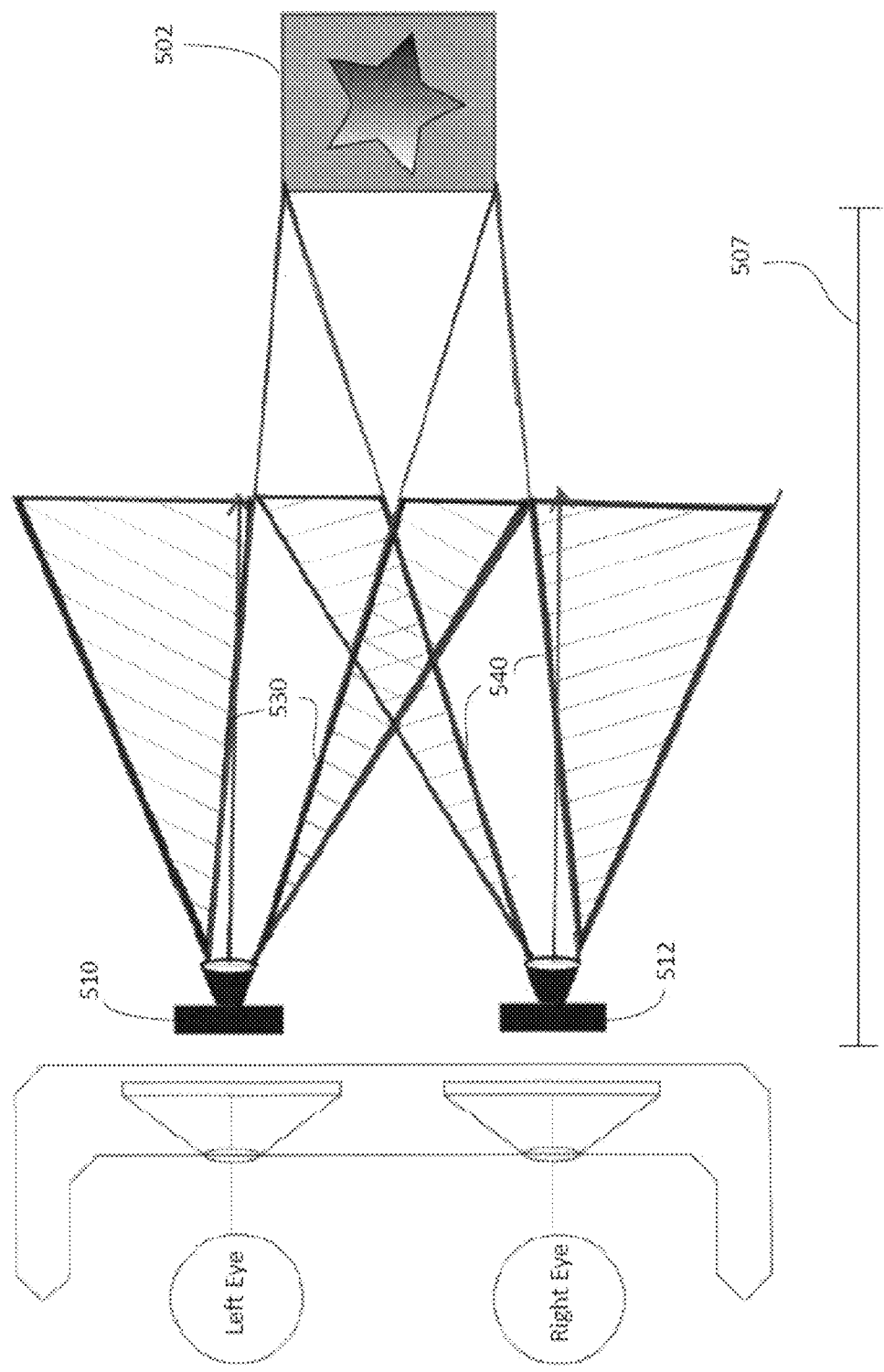
FIGS. 5A and 5B show schematic diagrams of a convergence technique implemented by a head-mounted display in accordance with an example embodiment of the present disclosure.
Figure 5B:
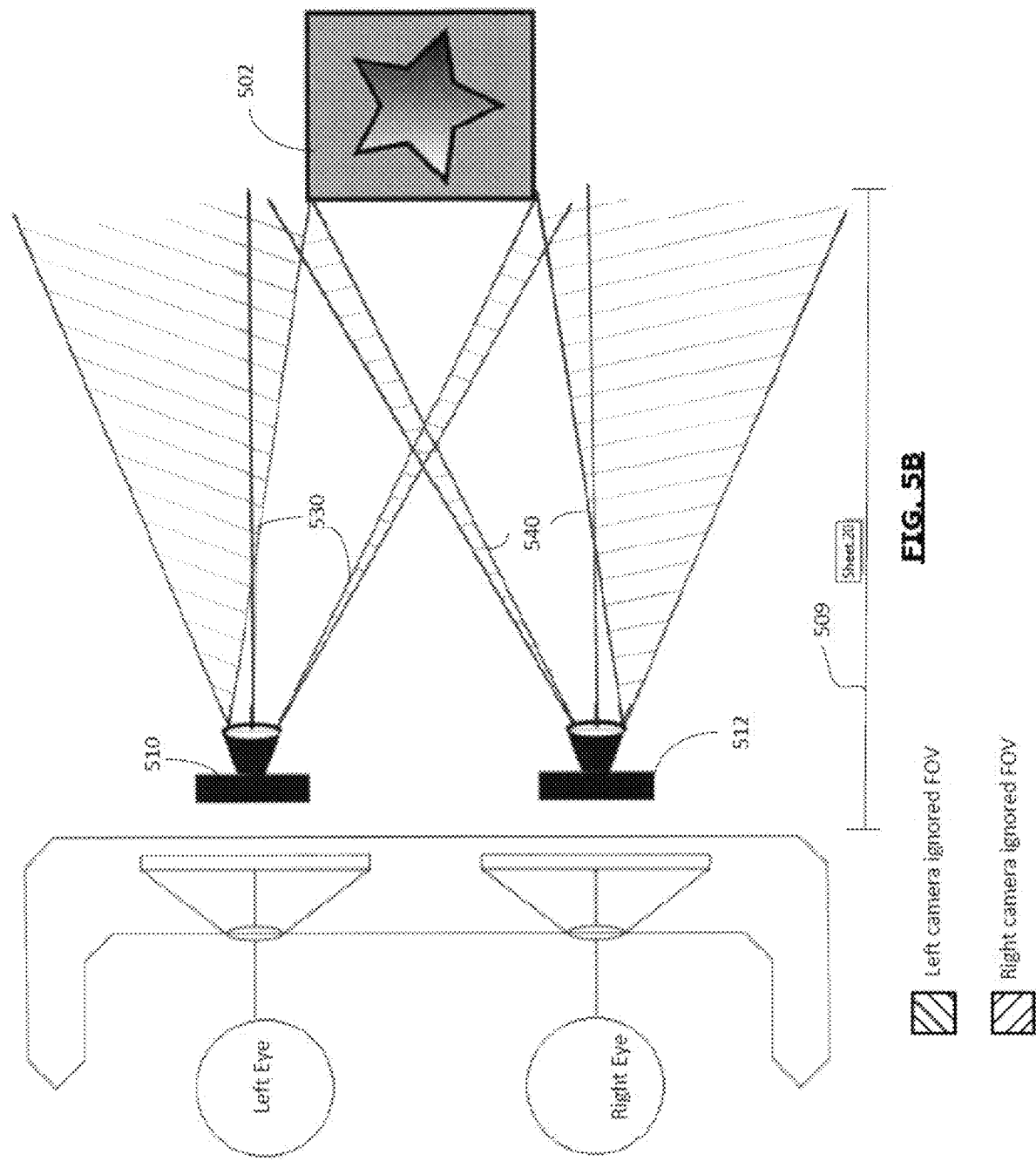

FIGS. 5A and 5B show schematic diagrams illustrating a convergence technique implemented by an HMD in accordance with example embodiments of the present disclosure. In FIG. 5A, the distance to an object of interest 502 is denoted by 507, which is greater than the distance to the object of interest 502 in FIG. 5B, denoted by 509. For example, FIG. 5B models a scenario in which an object of interest is brought closer to the cameras 510 and 512 than in FIG. 5A. Dynamic/automatic convergence may be effected by displaying shifted sub-images of images captured by the cameras, following the change in distance to the object of interest. More specifically, as can be seen in FIG. 5B, a first sub-image of an image of a scene captured by the left camera 510 is shifted to the right (as illustrated by a rotation of display frustum 530) and a second sub-image of an image of the scene captured by the right camera 512 is shifted to the left (as illustrated by a rotation of display frustum 540), when the object of interest is moved closer to the cameras 510 and 512. In at least some embodiments, the amount of rotation of display frustums 530 and 540 required for proper convergence may be calculated based on the focal distance (as a proxy for distance to the object of interest) and the known geometry defined by the positions of the cameras 510 and 512 and their respective fields of view.

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A head-mounted display, comprising:
   a first camera for capturing a left viewpoint image of a scene;
   a second camera for capturing a right viewpoint image of the scene, the second camera having a field of view at least partially overlapping a field of view of the first camera;
   a first display unit and a second display unit; and
   a processor coupled to the first camera, the second camera, the first display unit and the second display unit, the processor being configured to:
      receive a left-eye image from the first camera; receive a right-eye image from the second camera;
      identify a user-selected object of interest which is included in both the left-eye image and the right-eye image;
      select a first sub-image of the left-eye image such that the user-selected object of interest is displayed in a central position within the first sub-image;
      select a second sub-image of the second image such that the user-selected object of interest is displayed in a central position within the second sub-image;
      display, on the first display unit, a shifted first sub-image, the shifted first sub-image being modeled by a rotation of a first display frustum, wherein an amount of rotation of the first display frustum is calculated based on a focal distance, between the object of interest and the first camera, position of the first camera, and respective field of view of the first camera; and
      display, on the second display unit, a shifted second sub-image, the shifted second sub-image being modeled by a rotation of a second display frustum, wherein an amount of rotation of the second display frustum calculated based on a focal distance, between the object of interest and the second camera, position of the second camera, and respective field of view of the second camera.

2. The head-mounted display of claim 1, wherein fields of view of the first camera and the second camera are greater than fields of view of the first display unit and the second display unit, respectively.

3. The head-mounted display of claim 1, wherein the first sub-image and the second sub-image are displayed at magnification levels greater than magnification levels for the first image and the second image, respectively.

4. The head-mounted display of claim 1, wherein updating the displays on the first and second display units comprises shifting the first sub-image to the right and shifting the second sub-image to the left, respectively.

5. A processor-implemented method comprising:
   receiving a left-eye image from a first camera for capturing a left viewpoint image of a scene;
   receiving a right-eye image from a second camera for capturing a right viewpoint image of the scene, the second camera having a field of view at least partially overlapping a field of view of the first camera;
   identifying a user-selected object of interest which is included in both the left-eye image and the right-eye image;
   selecting a first sub-image of the left-eye image such that the user-selected object of interest is displayed in a central position within the first sub-image;
   selecting a second sub-image of the second image such that the user-selected object of interest is displayed in a central position within the second sub-image;
   displaying, on the first display unit, a shifted first sub-image, the shifted first sub-image being modeled by a rotation of a first display frustum, wherein an amount of rotation of the first display frustum is calculated based on a focal distance, between the object of interest and the first camera, position of the first camera, and respective field of view of the first camera; and
   displaying, on the second display unit, a shifted second sub-image, the shifted second sub-image being modeled by a rotation of a second display frustum, wherein an amount of rotation of the second display frustum calculated based on a focal distance, between the object of interest and the second camera, position of the second camera, and respective field of view of the second camera.

6. The method of claim 5, wherein fields of view of the first camera and the second camera are greater than fields of view of the first display unit and the second display unit, respectively.

7. The method of claim 5, wherein the first sub-image and the second sub-image are displayed at magnification levels greater than magnification levels for the first image and the second image, respectively.

8. The method of claim 5, wherein updating the displays on the first and second display units comprises shifting the first sub-image to the right and shifting the second sub-image to the left, respectively.

* * * * *